(12) United States Patent
Dong et al.

(10) Patent No.: US 10,646,272 B2
(45) Date of Patent: May 12, 2020

(54) RADIO-FREQUENCY ABLATION CATHETER HAVING SPIRAL STRUCTURE AND DEVICE THEREOF

(71) Applicant: SHANGHAI GOLDEN LEAF MED TEC CO., LTD., Shanghai (CN)

(72) Inventors: Yonghua Dong, Shanghai (CN); Meijun Shen, Shanghai (CN); Liang Ji, Shanghai (CN); Jun Jiang, Shanghai (CN)

(73) Assignee: SHANGHAI GOLDEN LEAF MED TEC CO., LTD., Shanghai (CN)

( * ) Notice: Subject to any disclaimer, the term of this patent is extended or adjusted under 35 U.S.C. 154(b) by 181 days.

(21) Appl. No.: 15/548,672

(22) PCT Filed: Feb. 3, 2016

(86) PCT No.: PCT/CN2016/073378
§ 371 (c)(1),
(2) Date: Aug. 3, 2017

(87) PCT Pub. No.: WO2016/124138
PCT Pub. Date: Aug. 11, 2016

(65) Prior Publication Data
US 2017/0354462 A1    Dec. 14, 2017

(30) Foreign Application Priority Data

Feb. 3, 2015  (CN) .......................... 2015 1 0057095
Mar. 23, 2015 (CN) .......................... 2015 1 0129947
(Continued)

(51) Int. Cl.
*A61B 18/14* (2006.01)
*A61B 18/12* (2006.01)
*A61B 17/00* (2006.01)
*A61B 18/00* (2006.01)

(52) U.S. Cl.
CPC .......... *A61B 18/1492* (2013.01); *A61B 18/12* (2013.01); *A61B 2017/00862* (2013.01);
(Continued)

(58) Field of Classification Search
CPC .... A61B 2018/0094; A61B 2018/1435; A61B 2018/1465; A61B 2018/1467;
(Continued)

(56) References Cited

U.S. PATENT DOCUMENTS 6,613,046 B1 * 9/2003 Jenkins .............. A61B 18/1492
600/374
7,850,685 B2 * 12/2010 Kunis ................ A61B 18/1815
606/41
(Continued)

FOREIGN PATENT DOCUMENTS

CN    101309651 A    11/2008
CN    201469401 U    5/2010
(Continued)

Primary Examiner — Michael F Peffley
Assistant Examiner — Amanda L Zink
(74) Attorney, Agent, or Firm — Kirton McConkie; Evan R. Witt

(57) ABSTRACT

Disclosed are a radio-frequency ablation catheter having a spiral structure and device thereof. The radio-frequency ablation catheter has an elongated catheter body. A spiral electrode support is arranged at the front end of the catheter body. Multiple electrodes are arranged on the electrode support. A control handle is arranged at the rear end of the catheter body. Wall-attachment adjusting wires having various structures can be arranged in the radio-frequency ablation catheter, so that the radio-frequency ablation catheter having a spiral structure can be adapted to target vessels of different diameters, and so that the electrodes on the electrode support have a good wall-attachment state.

14 Claims, 14 Drawing Sheets

(30) Foreign Application Priority Data

| Jun. 19, 2015 | (CN) | 2015 1 0349237 |
| Jun. 19, 2015 | (CN) | 2015 1 0350172 |
| Jun. 19, 2015 | (CN) | 2015 2 0433569 U |
| Jun. 19, 2015 | (CN) | 2015 2 0434410 U |

(52) U.S. Cl.
CPC ............. *A61B 2018/0094* (2013.01); *A61B 2018/00196* (2013.01); *A61B 2018/00577* (2013.01); *A61B 2018/1435* (2013.01); *A61B 2018/1465* (2013.01); *A61B 2018/1467* (2013.01); *A61B 2018/1475* (2013.01)

(58) Field of Classification Search
CPC ........... A61B 2018/1475; A61B 18/12; A61B 18/1492; A61B 2017/00862; A61B 2018/00196; A61B 2018/00577
See application file for complete search history.

(56) References Cited

U.S. PATENT DOCUMENTS

| 2009/0264770 A1* | 10/2009 | Liu | A61B 17/22012 |
| | | | 600/466 |
| 2012/0116382 A1* | 5/2012 | Ku | A61B 18/1492 |
| | | | 606/33 |
| 2013/0304062 A1* | 11/2013 | Chan | A61B 18/1492 |
| | | | 606/41 |
| 2014/0276748 A1* | 9/2014 | Ku | A61B 18/18 |
| | | | 606/33 |
| 2014/0309524 A1 | 10/2014 | Vetter | |
| 2016/0256216 A1* | 9/2016 | Chang | A61B 18/1492 |
| 2017/0027640 A1 | 2/2017 | Kunis et al. | |

FOREIGN PATENT DOCUMENTS

| CN | 102488552 A | 6/2012 |
| CN | 203280485 U | 11/2013 |
| CN | 103830001 A | 6/2014 |
| CN | 104605930 A | 5/2015 |
| CN | 104688334 A | 6/2015 |
| CN | 104939918 A | 9/2015 |
| CN | 204734547 U | 11/2015 |
| CN | 105193497 A | 12/2015 |
| CN | 204971568 U | 1/2016 |

* cited by examiner

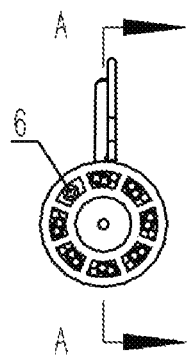 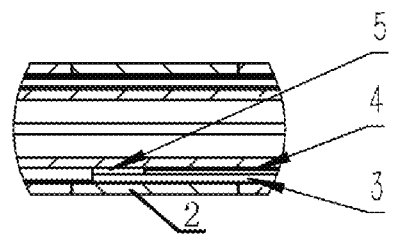
FIG 15    FIG 17
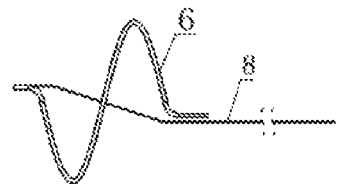
FIG 18
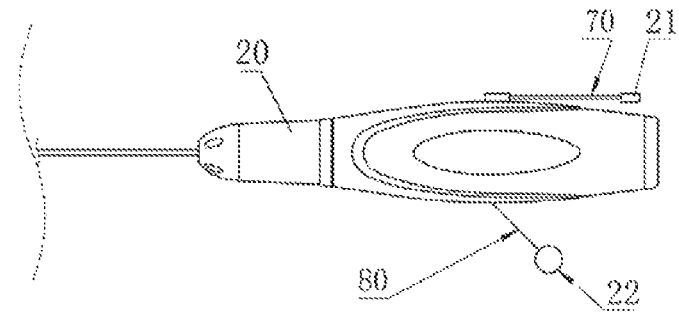
FIG 19

RADIO-FREQUENCY ABLATION CATHETER HAVING SPIRAL STRUCTURE AND DEVICE THEREOF

BACKGROUND

Technical Field

The present invention relates to the technical field of interventional medical devices, and relates to a radio-frequency ablation catheter having a spiral structure, and to a radio-frequency ablation device including the radio-frequency ablation catheter.

Related Art

In a radio-frequency ablation system, a radio-frequency ablation catheter is a key component for entering a human vessel and releasing radio-frequency energy. A radio-frequency electrode is installed on a support at a front end of the radio-frequency ablation catheter, and the support is used for carrying the radio-frequency electrode, and expands to perform wall attachment before radio frequency ablation begins and retracts and withdraws after radio frequency ablation ends. Because a radio-frequency surgery is performed by directly entering a human vessel, a telescopic size of the support needs to adapt to a diameter of a human vessel.

Diameters of human vessels vary with different ablation parts. In addition, diameters of human vessels also vary from person to person. For example, a diameter of a renal artery is approximately within a range from 2 mm to 12 mm, and has a great difference. In the prior art, generally, a telescopic size of an electrode end of a radio-frequency ablation catheter is fixed, and cannot adapt to requirements of diameters of different human vessels, and coverage on human vessels of different diameters is relatively small. Therefore, when radio-frequency surgeries are performed on different patients, generally, radio-frequency ablation catheters of different specifications and models need to be changed. Even so, in some cases, a problem that radio-frequency electrodes cannot perform wall attachment at the same time during a surgery may occur, affecting an effect of the surgery.

A structure of a radio-frequency ablation catheter is classified into multiple types according to shapes of an electrode and an electrode support, such as a saccule-type structure, a puncture needle-type structure, a spiral structure, or a flap-like structure. A radio-frequency ablation catheter for which an electrode support is designed to be spiral is used widely.

For an existing spiral radio-frequency ablation catheter, mainly, an electrode support is shaped in advance, and then, the radio-frequency ablation catheter enters the interior of a vessel with assistance of a guiding catheter/a sheath. The radio-frequency ablation catheter is moved forward or the guiding catheter/sheath is moved backward, to remove the radio-frequency ablation catheter from the sheath/guiding catheter, so that the electrode support restores to a shaped shape after entering a target location. For a single radio-frequency ablation catheter, a size for shaping an electrode support in advance is fixed. Therefore, adaptability of the existing spiral radio-frequency ablation catheter to vessels of different diameters is limited.

SUMMARY

The first technical problem to be resolved by the present invention is to provide an improved radio-frequency ablation catheter having a spiral structure.

Another technical problem to be resolved by the present invention is to provide a radio-frequency ablation device including the foregoing radio-frequency ablation catheter.

To achieve the foregoing objectives of the present invention, the following technical solutions are used in the present invention:

A radio-frequency ablation catheter having a spiral structure includes an elongated catheter body, where an electrode support of a spiral shape is disposed at a front end of the catheter body, multiple electrodes are disposed on the electrode support, and a control handle is disposed at a rear end of the catheter body, where a slidable support wall-attachment adjusting wire is disposed in one lumen in the electrode support and the catheter body, and the support wall-attachment adjusting wire consists of a flexible section that is far away from the control handle and a rigid section that is close to the control handle.

Preferably, a head end of the support wall-attachment adjusting wire penetrates through the electrode support, then is limited at the outside of the electrode support, and can move, relative to a far end of the electrode support, towards a direction that is far away from the catheter; a tail end of the support wall-attachment adjusting wire penetrates through the catheter body and is fixed on the control handle; and the control handle is used to control the support wall-attachment adjusting wire to move forward and backward.

Preferably, when the support wall-attachment adjusting wire moves forward to make the rigid section be in the electrode support and the flexible section be at the outside of electrode support, under the effect of the rigid section of the support wall-attachment adjusting wire, a diameter of the spiral shape of the electrode support is reduced, a length is increased and the spiral shape tends to be a straight-line shape; and when the support wall-attachment adjusting wire withdraws to make the flexible section be in the electrode support, the electrode support restores to the spiral shape.

Preferably, a button control component that is fixed with the tail end of the support wall-attachment adjusting wire is disposed on the control handle, and the support wall-attachment adjusting wire is controlled to move by changing a location of the button control component on the control handle.

Preferably, a developing head is disposed at the head end of the support wall-attachment adjusting wire.

Preferably, the support wall-attachment adjusting wire has a bifurcated adjusting wire that extends backward; a head end of the bifurcated adjusting wire is fixed at the head end of the support wall-attachment adjusting wire, or a head end of the bifurcated adjusting wire is fixed at a particular part of the flexible section, or the bifurcated adjusting wire is a thin filament that is bifurcated from the flexible section to the outside; and a rear end of the bifurcated adjusting wire penetrates out of a hole provided on an outer tube on the electrode support, penetrates into a hole provided on the electrode support or the catheter body, then extends to the outside of the catheter with the rigid section of the support wall-attachment adjusting wire side by side along a lumen in the catheter body, enters the interior of the control handle, and is fixed on a second control component.

Preferably, the electrode support includes an outer tube, multiple electrodes are embedded on an outer circumference of the outer tube, multiple lumens are disposed in the outer tube, one group of thermocouple wires and radio-frequency lines is disposed in each of some lumens, one group of radio-frequency lines and thermocouple wires is disposed in each electrode, the radio-frequency line is connected to the electrode, and the thermocouple wire and the electrode are disposed in an insulation manner.

Preferably, a spiral shaped wire is disposed in the electrode support.

A radio-frequency ablation catheter having a spiral structure includes an elongated catheter body, where an electrode support of a spiral shape is disposed at a front end of the catheter body, one or more electrodes are disposed on the electrode support, and a control handle is disposed at a rear end of the catheter body, where a rear section of the wall-attachment adjusting wire is slidably disposed in one lumen in the catheter body; a rear end of the wall-attachment adjusting wire is connected to a control component disposed on the control handle, or a rear end of the wall-attachment adjusting wire penetrates through the control handle and then is connected to a control component on a peripheral device; and a front section of the wall-attachment adjusting wire penetrates out of the electrode support and then is exposed outside the electrode support, and a front end of the wall-attachment adjusting wire returns to the interior of the electrode support and is fixed.

Preferably, the front end of the wall-attachment adjusting wire returns to the interior of the electrode support, then returns to the rear end of the catheter body through a lumen in the electrode support and the catheter body, and is fixed on the control handle or is fixed on the control component.

Alternatively, preferably, the front end of the wall-attachment adjusting wire returns to the interior of the electrode support, and then is fixed at a front end of the electrode support.

Alternatively, preferably, the front end of the wall-attachment adjusting wire returns to the interior of the electrode support, and then penetrates out of the front end of the electrode support and is fixed or limited at the outside; and the wall-attachment adjusting wire is also a support wire.

Alternatively, preferably, the radio-frequency ablation catheter having a spiral structure further includes: a support wire disposed in a particular lumen in a connecting duct and the electrode support, where the front end of the wall-attachment adjusting wire is fixed on the support wire; or the wall-attachment adjusting wire is a thin filament that is of the support wire and that is bifurcated to the outside.

Preferably, a part of the support wire in the electrode support is shaped to a spiral shape, to form a spiral shaped section.

Alternatively, preferably, there is a fixing point between a part of the wall-attachment adjusting wire that is exposed outside the electrode support and the electrode support; and the front end and the rear end of the wall-attachment adjusting wire respectively penetrate out of the rear end of the catheter body and are fixed on corresponding control components disposed on the control handle, or the front end and the rear end of the wall-attachment adjusting wire respectively penetrate out of the rear end of the catheter body and penetrate through the control handle and then are connected to corresponding control components on the peripheral device.

Preferably, a particular point of the wall-attachment adjusting wire that is exposed outside the electrode support is fixed in a hole in a particular spiral section of the electrode support.

Alternatively, preferably, the wall-attachment adjusting wire is formed by multiple strands of wires; a front end of each strand of wire is fixed on the electrode support; a rear end is wound around a spiral section of the electrode support from the outside and then enters the interior of the electrode support or the catheter body, and then penetrates out of the end of the catheter body through a lumen in the catheter body, and is fixed on a corresponding control component disposed on the control handle or penetrates through the control handle and then is connected to a corresponding control component on the peripheral device; and the multiple strands of wires are respectively used to independently control diameters of different spiral sections of the electrode support.

Preferably, fixing points of the multiple strands of wires on the electrode support are different from each other.

Preferably, in the multiple strands of wires, every two strands of wires have a common fixing point on the electrode support.

Preferably, each strand of wire enters the interior of the electrode support from a different location on the electrode support.

Alternatively, preferably, fixing points of the multiple strands of wires on the electrode support are the same.

A radio-frequency ablation device includes the foregoing radio-frequency ablation catheter and a radio-frequency ablation host connected to the radio-frequency ablation catheter.

According to the radio-frequency ablation catheter provided in the present invention, support wall-attachment adjusting wires having different structures or wall-attachment adjusting wires having different structures are disposed, so that the radio-frequency ablation catheter having a spiral structure can adapt to target lumens of different diameters, and wall-attachment states of electrodes on an electrode support are good. In the target lumens of different diameters, the wall-attachment adjusting wires are pulled, so that the wall-attachment states of the electrodes disposed on the electrode support are good. In addition, the wall-attachment adjusting wire may also use a multi-strand structure, and a single wire is independently controlled, so that different spiral sections of the radio-frequency ablation catheter can be respectively controlled, thereby reducing a difficulty of adjusting a diameter of the electrode support.

BRIEF DESCRIPTION OF THE DRAWINGS

FIG. 1a is a schematic structural diagram of a radio-frequency ablation catheter having a spiral structure according to a first embodiment;

FIG. 1b is a schematic side view of the radio-frequency ablation catheter shown in FIG. 1a;

FIG. 1c is a schematic structural diagram of a control handle in the radio-frequency ablation catheter shown in FIG. 1a;

FIG. 6b is a schematic side view of the radio-frequency ablation catheter shown in FIG. 6a;

FIG. 15 is a schematic cross-sectional view of the electrode support in the radio-frequency ablation catheter having a spiral structure shown in FIG. 14;

FIG. 17 is a schematic enlarged view of an II part of the radio-frequency ablation catheter having a spiral structure shown in FIG. 16;

FIG. 18 is a schematic diagram of another manner in which an wall-attachment adjusting wire is disposed in the radio-frequency ablation catheter having a spiral structure according to the second embodiment;

FIG. 19 is a schematic structural diagram of a control handle in the radio-frequency ablation catheter having a spiral structure according to the second embodiment;

DETAILED DESCRIPTION

Technical content of the present invention is described in detail below with reference to the accompanying drawings and specific embodiments.

First Embodiment

Figures 1A, 1B:
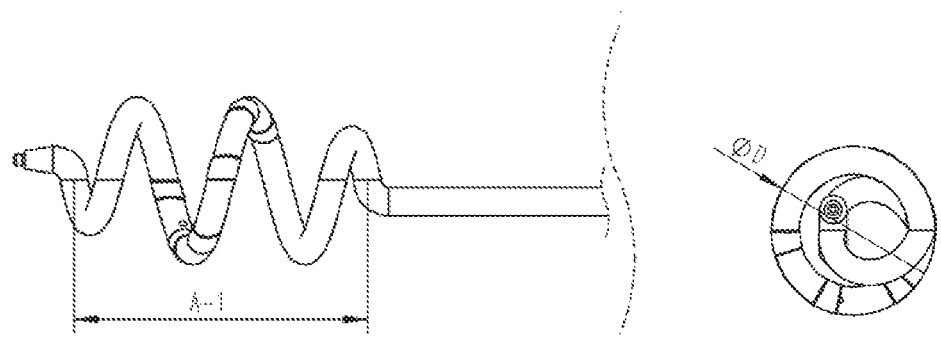
Figure 1C:
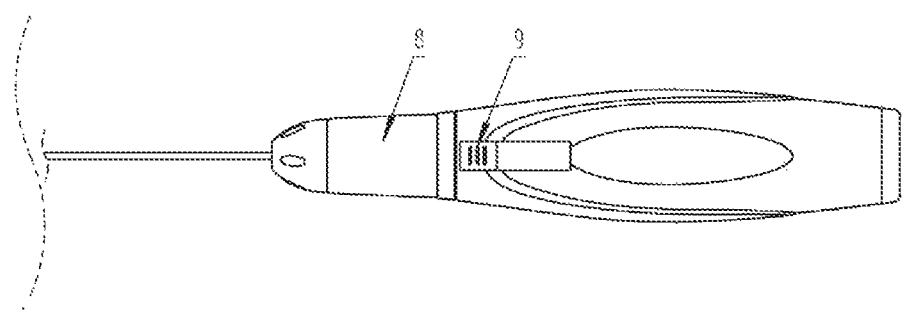

As can be learned with reference to FIG. 1a to FIG. 1c, a radio-frequency ablation catheter having a spiral structure that is provided in the present invention includes an elongated catheter body. An electrode support of a spiral shape is disposed at a front end of the catheter body. An initial diameter of the spiral shape of the electrode support is ΦD, and an initial length is A-1 (referring to FIG. 1a and FIG. 1b), and preferably, ΦD should be greater than a diameter of a target lumen. A control handle 8 is disposed at a rear end of the catheter body (referring to FIG. 1c). During actual manufacturing, the electrode support may be integrally manufactured with the catheter body, and the electrode support is a part of a spiral shape at the front end of the catheter body. Alternatively, the electrode support may be manufactured independently, and then is integrally connected to the catheter body. The electrode support of the spiral shape includes an outer tube 1 and multiple electrodes 2 disposed on the outer tube 1. The electrode 2 may be a block electrode or an annular electrode embedded on an outer circumference of the outer tube 1, and an upper surface of the electrode 2 may be flush with an outer surface of the outer tube 1 or is slightly higher than an outer surface of the outer tube 1, or an upper surface of the electrode 2 may be lower than an outer surface of the outer tube 1.

A lumen used to accommodate a support wall-attachment adjusting wire 6 is disposed in the electrode support and the catheter body. Support wall-attachment adjusting wires 6 are disposed in corresponding lumens in the electrode support and the catheter body (referring to FIG. 2). The support wall-attachment adjusting wires 6 may slide forward and backward in the corresponding lumens in the electrode support and the catheter body, and the lumen used to accommodate the support wall-attachment adjusting wire 6 may be a central hole in the electrode support or the catheter body, or may be one of multiple lumens distributed in the periphery of the center. As shown in FIG. 1a, a head end of the support wall-attachment adjusting wire 6 penetrates through the electrode support, then is limited at the outside of the electrode support, and can move, relative to a far end of the electrode support, towards a direction that is far away from the catheter body. A developing head 63 is disposed at a head end of the support wall-attachment adjusting wire 6. As shown in FIG. 1c, a tail end of the support wall-attachment adjusting wire 6 penetrates through the central hole in the catheter body and is fixed on the control handle 8. The control handle 8 is used to control the support wall-attachment adjusting wire 6 to move forward and backward. A button control component 9 is disposed on the control handle 8. The tail end of the support wall-attachment adjusting wire 6 penetrates through the central hole in the catheter body and then is fixed on the button control component 9. The support wall-attachment adjusting wire 6 is controlled to move forward and backward by changing a location of the button control component 9 on the control handle 8.

Figure 3:
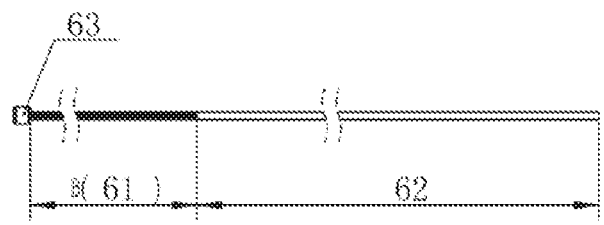
FIG. 3 is a schematic structural diagram of a first type of support wall-attachment adjusting wire in the radio-frequency ablation catheter having a spiral structure according to the first embodiment.

For the radio-frequency ablation catheter having a spiral structure, a diameter of the electrode support is changed by improving a structure of the support wall-attachment adjusting wire 6, so that the electrode support is easy to be inserted to a guiding catheter/a sheath and a target lumen; in addition, after the electrode support reaches the target lumen, the electrode support can be restored to the natural spiral shape. As shown in FIG. 3, in the radio-frequency ablation catheter, the support wall-attachment adjusting wire 6 includes two parts: a flexible section 61 that is far away from the control handle 8 (close to the head end) and a rigid section 62 that is close to the control handle 8 (close to the tail end). It is preferred that a length of the flexible section 61 is not less than a length of the outer tube 1 of the electrode support. Certainly, in a special case, the length of the flexible section 61 may be less than the length of the outer tube 1 of the electrode support. The diameter of the spiral shape of the electrode support may be changed by changing, by using the control handle 8, an area in which the support wall-attachment adjusting wire 6 coincides with the electrode support.

Figure 4:
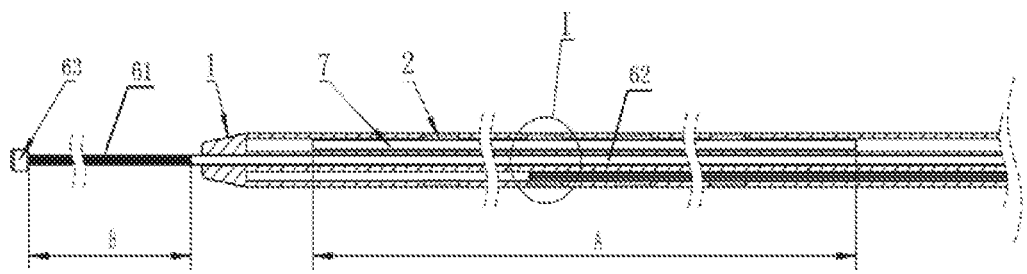
FIG. 4 is a schematic diagram of a D-D section of the radio-frequency ablation catheter having a spiral structure when a rigid section of the support wall-attachment adjusting wire coincides with the electrode support.
Figure 6A:
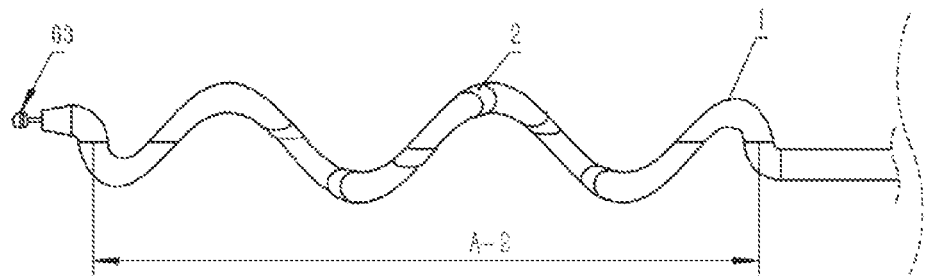
FIG. 6a is a schematic structural diagram of the radio-frequency ablation catheter having a spiral structure when a flexible section of the support wall-attachment adjusting wire coincides with the electrode support.
Figure 6B:
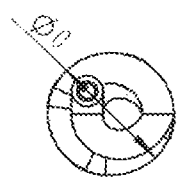
Figure 7A:
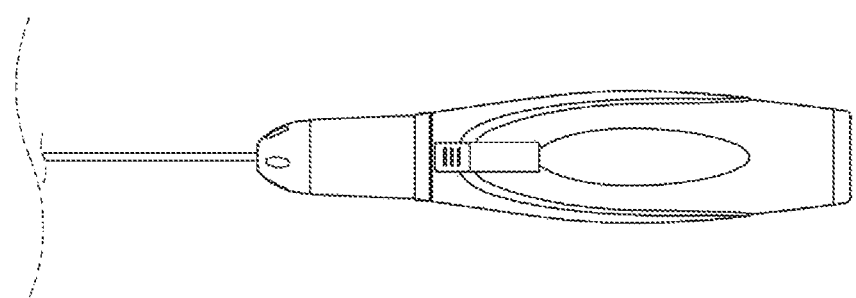
FIG. 7a is a schematic state diagram of a control handle when a button control component moves forward to feed a wire, and a rigid section of a control line coincides with the electrode support.
Figure 7B:
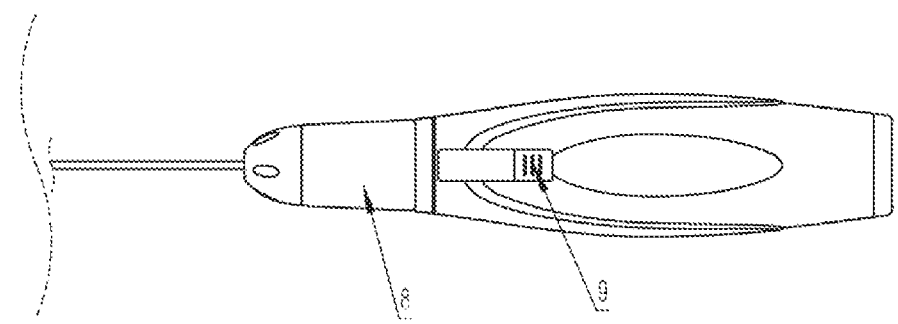
FIG. 7b is a schematic state diagram of the control handle when the button control component moves backward to pull a wire, and a flexible section of the control line coincides with the electrode support.

When the support wall-attachment adjusting wire 6 moves forward to make the rigid section 62 of the support wall-attachment adjusting wire 6 be in the electrode support and the flexible section 61 of the support wall-attachment adjusting wire 6 be at the outside of electrode support, under the effect of the rigid section 62 of the support wall-attachment adjusting wire 6, the diameter of the spiral shape of the electrode support is reduced, a length is increased, and the spiral shape tends to be a straight-line shape. In an ideal case, the electrode support may present a straight-line shape shown in FIG. 4. When the support wall-attachment adjusting wire 6 retracts to make the flexible section 61 of the support wall-attachment adjusting wire 6 enter the electrode support, the electrode support is gradually bent with entering by the flexible section. The electrode support restores to the spiral shape until the rigid section 62 is not in the electrode support and only the flexible section 61 is in the electrode support (referring to FIG. 6a). A diameter ΦC thereof is equal to or is approximate to a diameter of a target lumen (referring to FIG. 6b). In this case, the length A-2 of the spiral shape of the electrode support is greater than the initial length A-1. That is, in the radio-frequency ablation catheter, the support wall-attachment adjusting wire 6 is controlled to move forward, so that the rigid section 62 of the support wall-attachment adjusting wire 6 coincides with the outer tube 1 of the electrode support, to reduce the diameter of the spiral shape of the electrode support. Therefore, the electrode support is suitable for entering a guiding catheter/a sheath or a target lumen. In addition, when the electrode support reaches a target lumen, the support wall-attachment adjusting wire 6 is pulled backward, so that the flexible section 62 of the support wall-attachment adjusting wire 6 coincides with the outer tube 1 of the electrode support, to make the electrode support restore to the spiral shape, thereby implementing wall attachment. A location of the button control component 9 on the control handle 8 may be shown in FIG. 7a and FIG. 7b. When the button control component 9 moves to a location at the left side, the flexible section 61 is exposed, and the rigid section 62 coincides with the outer tube 1 of the electrode support. When the button control component 9 moves to a location at the right side, the flexible section 61 of the support wall-attachment adjusting wire 6 coincides with the outer tube of the electrode support.

In addition, when the electrode support naturally expands to perform wall attachment, a wall attachment status of the electrode 2 may be further adjusted slightly by further pulling the support wall-attachment adjusting wire 6, so that the electrode 2 is in close contact with a vessel wall, thereby improving a wall-attachment state of the electrode 2. For the foregoing radio-frequency ablation catheter, the support wall-attachment adjusting wire 6 is disposed in the electrode support. After the flexible section 61 of the support wall-attachment adjusting wire 6 coincides with the outer tube of the electrode support, the support wall-attachment adjusting wire 6 is pulled again, and a range of motion of the support wall-attachment adjusting wire 6 is relatively small. Therefore, the support wall-attachment adjusting wire 6 is only used to slightly adjust the shape of the electrode support. During selection of a radio-frequency ablation catheter, selection of a radio-frequency ablation catheter whose diameter ΦD of a spiral shape is greater than or is approximate to a diameter of a target lumen is recommended. In this way, in a process in which the electrode support automatically extends in the target lumen and restores to the spiral shape, under the effect of a vessel wall, close wall attachment can be implemented. The radio-frequency ablation catheter achieves a good wall attachment effect for a target lumen whose diameter is less than or equal to the initial diameter of the spiral shape. Because a diameter of a human renal artery vessel is within a range from 2 mm to 12 mm, to ensure that the radio-frequency ablation catheter has good adaptability to both large and small vessels, selection of a radio-frequency ablation catheter whose ΦD is greater than 12 mm is recommended for use.

Figure 10:
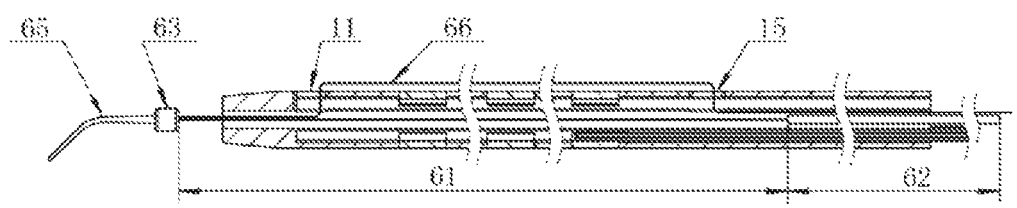
FIG. 10 is a schematic sectional view of the radio-frequency ablation catheter using a fourth type of support wall-attachment adjusting wire according to the first embodiment.
Figure 11:
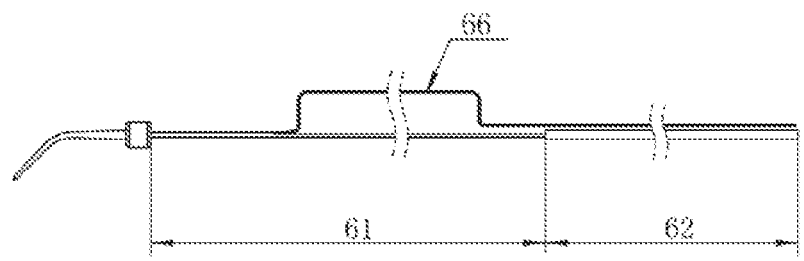
FIG. 11 is a schematic structural diagram of a fifth type of support wall-attachment adjusting wire in the radio-frequency ablation catheter having a spiral structure according to the first embodiment.
Figure 12:
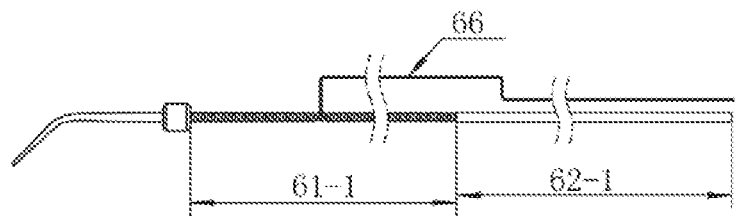
FIG. 12 is a schematic structural diagram of a sixth type of support wall-attachment adjusting wire in the radio-frequency ablation catheter having a spiral structure according to the first embodiment.

In addition, the present invention further provides a radio-frequency ablation catheter with a support wall-attachment adjusting wire 6 having a bifurcation (referring to FIG. 10, FIG. 11, and FIG. 12). In this case, the initial diameter ΦD of the spiral shape of the electrode support may be less than a diameter of a target lumen. The support wall-attachment adjusting wire 6 has a bifurcation that extends backward from the flexible section 61, that is, a bifurcated adjusting wire 66 in FIG. 10, FIG. 11, and FIG. 12. A head end of the bifurcated adjusting wire 66 is fixed at the head end of the support wall-attachment adjusting wire 6, or a head end of the bifurcated adjusting wire 66 is fixed at particular part of the flexible section 61, or the bifurcated adjusting wire 66 is a thin filament that is bifurcated from the flexible section 61 to the outside. A rear end of the bifurcated adjusting wire 66 penetrates out of a hole 11 provided on the outer tube 1 of the electrode support, penetrates into a hole 15 provided on the outer tube of the electrode support or a hole provided on the catheter body, then extends to the outside of the catheter with the support wall-attachment adjusting wire 6 side by side along a lumen in the catheter body, enters the interior of the control handle 8, and is fixed on a second control component on the control handle 8 (or an independently disposed second control component). When the foregoing radio-frequency ablation catheter having a spiral structure is used in a relatively large vessel, wall attachment cannot be performed after the electrode support restores to the natural spiral shape. In this case, the bifurcation (that is, the bifurcated adjusting wire 66) of the support wall-attachment adjusting wire 6 is pulled to increase the diameter of the spiral shape of the electrode support, so that the electrode support adapts to a vessel of a relatively large diameter. A structure and content related to this part are described in detail below.

Technical details of the radio-frequency ablation catheter having a spiral structure that is provided in the first embodiment are further described below.

Figure 2:
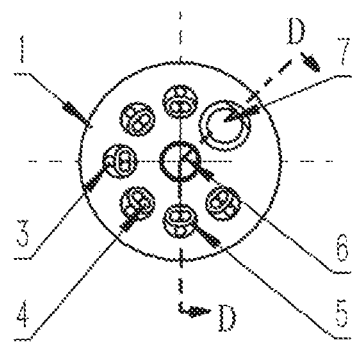
FIG. 2 is a schematic cross-sectional view of an electrode support in the radio-frequency ablation catheter having a spiral structure according to the first embodiment.
Figure 5:
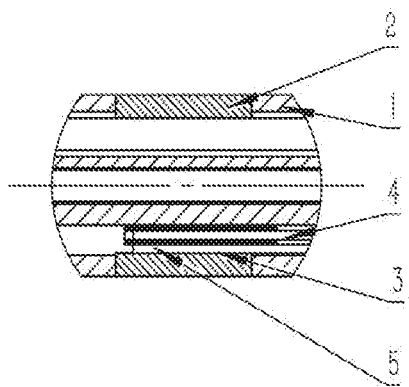
FIG. 5 is a schematic enlarged local view of an I part of the radio-frequency ablation catheter having a spiral structure shown in FIG. 4.

The outer tube 1 of the electrode support may be a single-lumen tube or a multi-lumen tube, and the outer tube 1 may be made of polymer materials or metal materials, for example, materials such as stainless steel or memory alloy. The outer tube 1 may be processed by using straight tube materials or bar materials, or may be made into a tube of a special shape by using an A section. As shown in FIG. 2 and FIG. 5, when the outer tube 1 uses a multi-lumen tube, in addition to the central hole, multiple lumens are further disposed in the outer tube 1 of the electrode support, one group of radio-frequency lines 3 and thermocouple wires 4 is disposed in each of some lumens, the thermocouple wire 4 is covered by a thermocouple wire head end insulation layer 5 to be separated from the radio-frequency line 3 and the electrode 2, head ends of each group of radio-frequency lines 3 and thermocouple wires 4 are disposed in a single electrode, a head end of the radio-frequency line 3 is closely soldered with the electrode 2, the head end of thermocouple wire 4 is soldered, and the head end of thermocouple wire 4 and the electrode 2 are disposed in an insulation manner. A spiral shaped wire 7 is further disposed in one lumen in the outer tube 1. The spiral shaped wire 7 is fixed on the A section in a spiral deformation area, and is used to support the spiral shape of the electrode support. Certainly, the electrode support may be directly shaped to the spiral shape, so that the spiral shaped wire 7 can be omitted. For example, when the outer tube is manufactured by using memory alloy, disposition of the spiral shaped wire 7 can be omitted.

The electrode 2 is fixed on the outer tube 1, and an outer surface of the electrode 2 may be lower than or may be not lower than the outer surface of the outer tube 1. The multiple electrodes 2 are evenly distributed or unevenly distributed on the spiral shape of the electrode support around a circumferential direction. The multiple electrodes may be distributed on the electrode support in one circle, more than one circle, or less than one circle. An inner surface of the electrode 2 is closely soldered with the radio-frequency line 3. Head ends of the thermocouple wires 4 are soldered together, the thermocouple wire head end insulation layer 5 is covered at a location at which the head end of the thermocouple wire 4 is soldered for insulation, and the head end of the thermocouple wire 4 is disposed in the electrode 2. The thermocouple wire head end insulation layer 5 may be a heat shrinkable tube or another casing.

Structures of multiple support wall-attachment adjusting wires applicable to the foregoing radio-frequency ablation catheter are described blow by using examples with reference to the accompanying drawings.

As shown in FIG. 3, a first type of support wall-attachment adjusting wire 6 provided in the present invention includes two parts: a flexible section 61 that is close to a head end and a rigid section 62. A developing head 63 may be disposed at a head end of the support wall-attachment adjusting wire 6, and is used to develop and image a target lumen.

Figure 8:
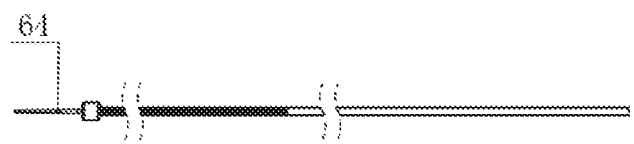
FIG. 8 is a schematic structural diagram of a second type of support wall-attachment adjusting wire in the radio-frequency ablation catheter having a spiral structure according to the first embodiment.
Figure 9:
FIG. 9 is a schematic structural diagram of a third type of support wall-attachment adjusting wire in the radio-frequency ablation catheter having a spiral structure according to the first embodiment.

Each of two types of support wall-attachment adjusting wires shown in FIG. 8 and FIG. 9 includes a flexible section 61 and a rigid section 62, and a straight-head flexible guide wire 64 or a curved-head flexible guide wire 65 is further disposed at a front end of the flexible section 61 of the support wall-attachment adjusting wire 6, so that the support wall-attachment adjusting wire 6 can directly enter a vessel by replacing a guiding catheter/a sheath, thereby simplifying operations in a surgery. Because a guiding catheter/a sheath is omitted, a diameter of the catheter that enters the vessel can be reduced greatly, which is convenient for the catheter to move.

Each of three types of support wall-attachment adjusting wires shown in FIG. 10 to FIG. 12 includes a bifurcated adjusting wire 66, and structures of the three types of bifurcated adjusting wires 66 are slightly different. Specifically, in a fourth type of support wall-attachment adjusting wire 6 shown in FIG. 10, a head end of the bifurcated adjusting wire 66 is fixed at a head end of the support wall-attachment adjusting wire 6, and then extends backward with the flexible section 61. A rear end of the bifurcated adjusting wire 66 penetrates out of the hole 11 provided on the outer tube 1 of the electrode support, penetrates into a corresponding lumen from the another hole 15 provided on the electrode support or the catheter body, then extends to the outside of the catheter with the support wall-attachment adjusting wire 6 side by side along a lumen in the catheter body, and is fixed on the second control component on the control handle 8.

In a fifth type of support wall-attachment adjusting wire 6 shown in FIG. 11, the head end of the bifurcated adjusting wire 66 is fixed at a particular part of the flexible section 61, or the bifurcated adjusting wire 66 is a thin filament that is bifurcated from the flexible section 61. Then, the rear end of the bifurcated adjusting wire 66 penetrates out of the hole provided on the outer tube 1 of the electrode support, penetrates into the another hole provided on the electrode support or the catheter body, then extends to the outside of the catheter with the support wall-attachment adjusting wire 6 side by side along a lumen in the catheter body, and is fixed on the second control component on the control handle.

In a sixth type of support wall-attachment adjusting wire 6 shown in FIG. 12, a manner in which the bifurcated adjusting wire is disposed is similar to that in a structure of the fourth type of support wall-attachment adjusting wire. A difference is that the flexible section uses a spring structure. The bifurcated adjusting wire 66 is a thin filament that is bifurcated from a particular part of a spring 61-1, and the head end of the bifurcated adjusting wire 66 is fixed on the spring. The rear end of the bifurcated adjusting wire 66 penetrates out of the hole provided on the outer tube 1 of the electrode support, penetrates into the another hole provided on the electrode support or the catheter body, then extends to the outside of the catheter with the rigid section 62-1 of the support wall-attachment adjusting wire 6 side by side along a lumen in the catheter body, enters the control handle 8, and is fixed on the second control component on the control handle.

Figure 13:
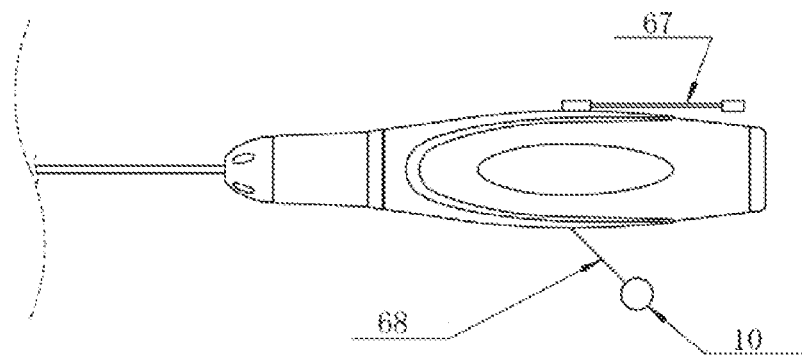
FIG. 13 is another schematic structural diagram of the control handle in the radio-frequency ablation catheter having a spiral structure according to the first embodiment.

By means of the foregoing three types of support wall-attachment adjusting wires, after the radio-frequency ablation catheter restores to the natural spiral shape in a vessel or a target lumen whose diameter is greater than the initial diameter ΦD of the spiral shape, and wall attachment still cannot be performed, the bifurcated adjusting wire 66 is pulled by using the second control component, to increase the diameter of the electrode support, so that the electrode can perform wall attachment. It should be noted that, a manner in which the second control component is disposed on the control handle 8 may be the same as a manner in which the button control component 9 is disposed. The second control component may also be independently disposed relative to the control handle 8, as in the embodiment shown in FIG. 13. After the bifurcated adjusting wire 66 and the support wall-attachment adjusting wire 6 enter the control handle 8 side by side, the end 67 of the support wall-attachment adjusting wire 6 is fixed on the button control component 9. A location of the button control component 9 on the control handle 8 can be changed by pushing the button control component 9, so as to change a form of the electrode support. The bifurcated adjusting wire 66 extends out of an opening provided on another side surface of the control handle 8, and the second control component 10 is fixed at the end 68 of the bifurcated adjusting wire 66. The diameter of the spiral shape of the electrode support can be further changed by pulling the second control component 10 at the outside of the control handle 8.

In the support wall-attachment adjusting wires shown in FIG. 10 to FIG. 12, flexible sections of multiple different structures are further respectively provided. The flexible section 61 of the support wall-attachment adjusting wire 6 in FIG. 10 has a same structure as the flexible sections in the first three types of support wall-attachment adjusting wires shown in FIG. 3, FIG. 8, and FIG. 9, and the flexible section 61 is constructed by using a thin filament or a flexible tube. The flexible section 61 may be made of a thin filament whose diameter is less than that of the rigid section. The flexible section 61 and the rigid section 62 may be integrally molded by using a same material or may be assembled by using two thin filaments of different diameters (for example, assembled by using a soldering process). The flexible section 61 may also be construed by using a flexible tube. In the support wall-attachment adjusting wire shown in FIG. 12, the flexible section 61-1 uses a spring structure. When the flexible section 61-1 is located in the electrode support, because a spring has a good flexural property, under the effect of the spiral shaped wire 7, the electrode support can restore to the spiral shape, and the flexible section 61-1 deforms accordingly.

The radio-frequency ablation catheter having a spiral structure that is provided in the first embodiment is described above. In this embodiment, the support wall-attachment adjusting wire in the radio-frequency ablation catheter having a spiral structure is improved by referring to the structure of the guide wire, but specific functions of the two are different. In the guide wire, the flexible section is used to initiatively adapt to a shape of a vessel. A direction of the guide wire is changed, so that the guide wire successfully reaches a target lumen. The rigid section is used to support the guide wire. In the radio-frequency ablation catheter having a spiral structure that is provided in the present invention, the form of the electrode support is changed by controlling the electrode support to coincide with different areas of the support wall-attachment adjusting wire 6, so that a difficulty of entering a guiding catheter/a sheath by the radio-frequency ablation catheter can be reduced, the structure is simple, and it is easy for an operation. When the support wall-attachment adjusting wire 6 moves forward to make the rigid section coincide with the spiral shape electrode support 2, under the effect of the rigid section of the support wall-attachment adjusting wire 6, the diameter of the spiral shape of the electrode support is reduced, the length is increased, and the spiral shape tends to be a straight-line shape, so that it is convenient for entering a guiding catheter/a sheath, and it is also convenient for the entire radio-frequency ablation catheter to move in a target lumen. When the support wall-attachment adjusting wire 6 withdraws to make the flexible section coincide with the spiral shape electrode support, the electrode support of the spiral shape restores to the spiral shape, and wall attachment can be performed. In addition, the wall-attachment state of the electrode can be further improved by continuously pulling the support wall-attachment adjusting wire backward. In addition, the straight-head flexible guide wire or the curved-head flexible guide wire is additionally disposed at the front end of the support wall-attachment adjusting wire, and the support wall-attachment adjusting wire can further directly enter a vessel by replacing a guiding catheter/a sheath, thereby simplifying operations in a surgery.

In addition, by means of the foregoing support wall-attachment adjusting wire, a difficulty of entering a human vessel by the radio-frequency ablation catheter is reduced, and an increased diameter of the electrode support of the spiral shape may be further changed by pulling the support wall-attachment adjusting wire, so that adaptability of the electrode support to target lumens of different diameters is relatively good.

In the radio-frequency ablation catheter having a spiral structure that is provided in the first embodiment, a support wall-attachment adjusting wire disposed in a particular lumen in the electrode support is used to adjust the diameter of the spiral shape of the electrode support. In other embodiments provided in the present invention, a wall-attachment adjusting wire that penetrates through or is wound around the electrode support may be disposed in the radio-frequency ablation catheter having a spiral structure, to adjust the increased diameter of the electrode support, so that adaptability of the electrode support to target lumens of different diameters is relatively good. For details, refer to the following descriptions.

Second Embodiment

As can be learned from FIG. 14 to FIG. 19, a radio-frequency ablation catheter having a spiral structure that is provided in the present invention includes an elongated catheter body. An electrode support of a spiral shape is disposed at a front end of the catheter body, and a control handle 20 is disposed at a rear end of the catheter body (referring to FIG. 19). During actual manufacturing, the electrode support may be integrally manufactured with the catheter body, and the electrode support is shaped to be a part of a spiral shape at the front end of the catheter body. The electrode support may also be manufactured independently, and then is integrally connected to the catheter body.

Figures 14, 16:
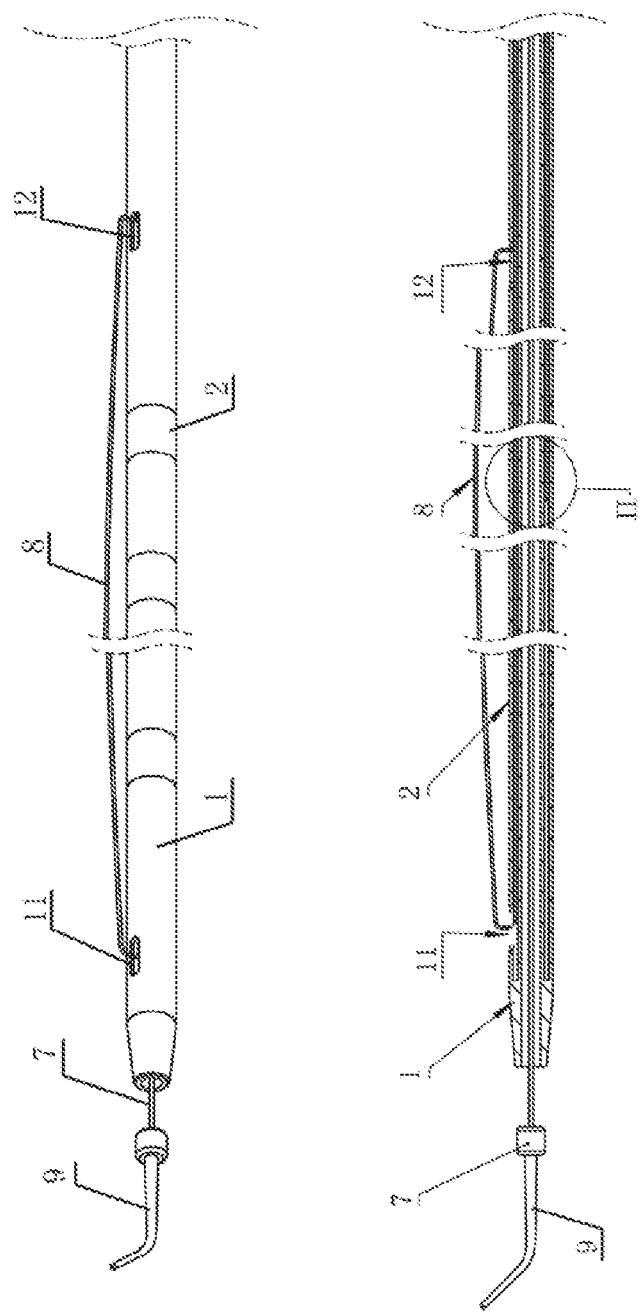
FIG. 14 is a schematic structural diagram of an electrode support and a catheter body in a radio-frequency ablation catheter having a spiral structure according to a second embodiment.
FIG. 16 is a schematic diagram of an A-A cross section of the radio-frequency ablation catheter having a spiral structure shown in FIG. 14.

As shown in FIG. 14, the electrode support of the spiral shape includes an outer tube 1 and one or more electrodes 2 disposed on the outer tube 1. The electrode 2 may be a block electrode or an annular electrode embedded on an outer circumference of the outer tube, and an upper surface of the electrode 2 may be flush with an outer surface of the outer tube 1 or is slightly higher than an outer surface of the outer tube 1, or an upper surface of the electrode 2 may be lower than an outer surface of the outer tube 1. The multiple electrodes 2 are evenly distributed or unevenly distributed on the spiral shape of the electrode support around a circumferential direction. The multiple electrodes may be distributed on the electrode support in one circle, more than one circle, or less than one circle.

The outer tube 1 of the electrode support may be a single-lumen tube or a multi-lumen tube, and the outer tube 1 may be made of polymer materials or metal materials, for example, materials such as stainless steel or memory alloy. The outer tube 1 may be processed by using straight tube materials or bar materials, or may be made into a tube of a special shape by using an A section. As shown in FIG. 15 and FIG. 17, when the outer tube 1 uses a multi-lumen tube, in addition to a central lumen, multiple lumens are disposed in the outer tube 1 of the electrode support, one group of radio-frequency lines 3 and thermocouple wires 4 is disposed in each of some lumens, head ends of each group of radio-frequency lines 3 and thermocouple wires 4 are disposed in a single electrode 2, a head end of the radio-frequency line 3 is closely fixed with the electrode 2, for example, connected by using a soldering process, a conductive adhesive adhesion process, or the like, head ends of two thermocouple wires 4 are soldered, are covered by a thermocouple wire head end insulation layer 5, and then the head ends of two thermocouple wires 4 and the radio-frequency line 3 and the electrode 2 are disposed in an insulation manner.

As shown in FIG. 15, a spiral shaped wire 6 is further disposed in one lumen in the outer tube 1. The spiral shaped wire 6 is fixed on a section in a spiral deformation area, and is used to support the spiral shape of the electrode support. Certainly, the electrode support may be directly shaped to the spiral shape, so that the spiral shaped wire 6 can be omitted. For example, when the outer tube is manufactured by using memory alloy or polymer materials, disposition of the spiral shaped wire 6 can be omitted.

As shown in FIG. 16, a support wire 7 is disposed in a central lumen in the catheter body and the electrode support, the support wire 7 may be movably disposed in the central lumen, or may be fixed in the central lumen, or the support wire 7 may be disposed in another lumen in the catheter body and the electrode support. A developing head may be disposed at a head end of the support wire 7, and is used to perform instant imaging on the interior of a target lumen. In addition, a flexible guide wire 9 may be disposed at a front end of the support wire 7. The flexible guide wire 9 may be a straight-head flexible guide wire or may be a curved-head flexible guide wire shown in the figure, so that the radio-frequency ablation catheter can directly enter a vessel without a guiding catheter/a sheath, thereby simplifying operations in a surgery.

As can be learned from FIG. 14 to FIG. 19, a lumen used to accommodate a wall-attachment adjusting wire 8 is further disposed the catheter body. A rear section of the wall-attachment adjusting wire 8 is slidably disposed in one lumen in the catheter body, and a rear end 80 of the wall-attachment adjusting wire 8 penetrates out of the catheter body and then penetrates into the control handle 20, and then penetrates out of the control handle 20 and is connected to a control component 22 on a peripheral device (referring to FIG. 19). The wall-attachment adjusting wire 8 may move forward and backward in the lumen in the catheter body. The lumen used to accommodate the wall-attachment adjusting wire 8 may be the central lumen, or may be one of multiple eccentric lumens distributed in the periphery of the central lumen. As shown in FIG. 14, a front section of the wall-attachment adjusting wire 8 penetrates out of a hole 12 that is close to a rear end of the electrode support to be at the outside of the electrode support and is exposed outside the electrode support; and a front end of the he wall-attachment adjusting wire 8 returns to the interior of the electrode support from a hole 11 that is close to a front end of the electrode support and is fixed.

A location at which the front end of the wall-attachment adjusting wire 8 is fixed may be different. The front end of the wall-attachment adjusting wire 8 may be fixed at the front end of the electrode support, or may be fixed at the front end of the support wire 7, or may be fixed on the spiral shaped wire 6, or may penetrate through a corresponding lumen in the electrode support and the catheter body and returns to the rear end of the catheter body, and is fixed on the control component 22 with the rear end of the wall-attachment adjusting wire 8.

Specifically, in a structure shown in FIG. 16, the front end of the wall-attachment adjusting wire 8 returns to the interior of the electrode support from the hole 11 that is close to the front end of the electrode support, and then returns to the rear end of the catheter body with the rear end of the wall-attachment adjusting wire 8 through a lumen in the electrode support and the catheter body. Then, the front end and the rear end of the wall-attachment adjusting wire 8 may be fixed together on a same control component 22 shown in FIG. 19, or for the front end and the rear end of the wall-attachment adjusting wire 8, one end is fixed on a housing of the control handle 20, and the other end is fixed on the control component 22. A diameter of a spiral section of the electrode support may be changed by pulling the control component 22.

Certainly, the front end of the wall-attachment adjusting wire 8 may also be simply fixed at the front end of the electrode support, or is fixed at the front end of the support wire 7 or a particular part that is of the support wire 7 and that is located in the electrode support, or is fixed at a particular part of the spiral shaped wire 6, or is fixed in a lumen in the electrode support, as long as the front end can be fixed. Therefore, when the wall-attachment adjusting wire 8 is pulled from the rear end, under the effect of the wall-attachment adjusting wire 8, the electrode support retracts and deforms, the diameter of the spiral shape of the electrode support is increased, and an axial distance between multiple spiral shapes is reduced. When the front end of the wall-attachment adjusting wire 8 is fixed on the support wire 7 or the spiral shaped wire 6, the wall-attachment adjusting wire 8 and the support wire 7/the spiral shaped wire 6 may be manufactured by using a same material. In this case, it may be understood that, the wall-attachment adjusting wire 8 is a thin filament that is bifurcated from the support wire 7/the spiral shaped wire 6 backward.

For example, in a structure shown in FIG. 18, the front end of the wall-attachment adjusting wire 8 is fixed with the front end of the spiral shaped wire 6. In this case, the spiral shaped wire 6 and the wall-attachment adjusting wire 8 may be manufactured by using a same thin filament, and the wall-attachment adjusting wire 8 and the spiral shaped wire 6 are respectively bifurcations of two thin filaments that are bifurcated from the front ends thereof backward. A bifurcation corresponding to the spiral shaped wire 6 is fixed in a particular lumen in the electrode support, and a rear section of a bifurcation corresponding to the wall-attachment adjusting wire 8 may slide in a lumen in the electrode support and/or the catheter body. When the wall-attachment adjusting wire 8 and the spiral shaped wire 6 are manufactured by using different materials (for example, the spiral shaped wire 6 uses a tube material, and the wall-attachment adjusting wire 8 uses a thin filament), the front end/the front section of the wall-attachment adjusting wire 8 and the spiral shaped wire 6 may be assembled together through soldering, riveting, adhesion, or the like.

In addition, as can be further learned from FIG. 19, in the foregoing structure, a button control component 21 is further disposed on the control handle 20. The end 70 of the support wire 7 penetrates out of the catheter body and then enters the control handle 20, and is fixed on the button control component 21. In addition to being disposed on the control handle 20 shown in the figure, the control component used to connect to the end of the support wire 7 may be further disposed at the outside of the control handle 20 as the control component 22. Similarly, the control component used to connect to the wall-attachment adjusting wire 8 may be also disposed on the control handle 20 as the button control component 21.

Figures 20A, 20B:
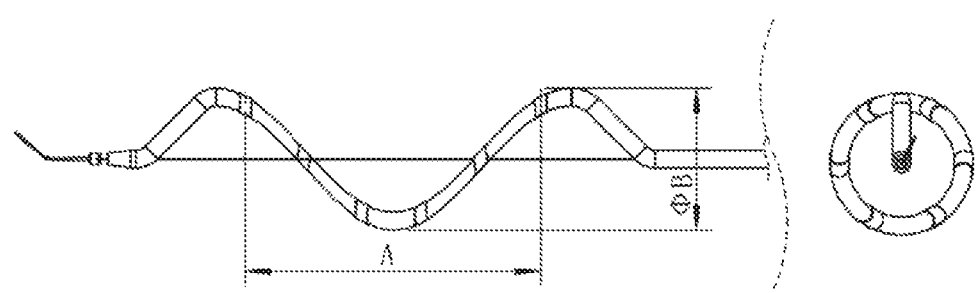
FIG. 20A is a schematic diagram of an initial state of the radio-frequency ablation catheter having a spiral structure shown in FIG. 14.
FIG. 20B is a schematic side view of the radio-frequency ablation catheter having a spiral structure shown in FIG. 20A.
Figure 21:
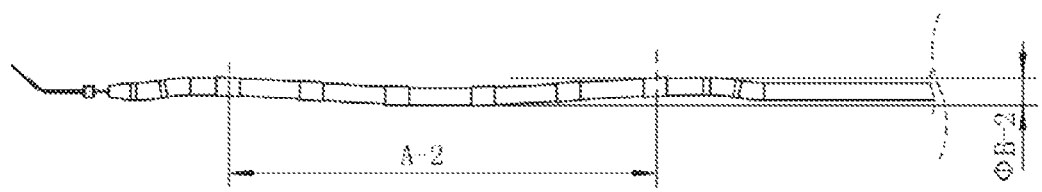
FIG. 21 is a schematic state diagram of the radio-frequency ablation catheter having a spiral structure shown in FIG. 14 in a sheath.
Figure 22:
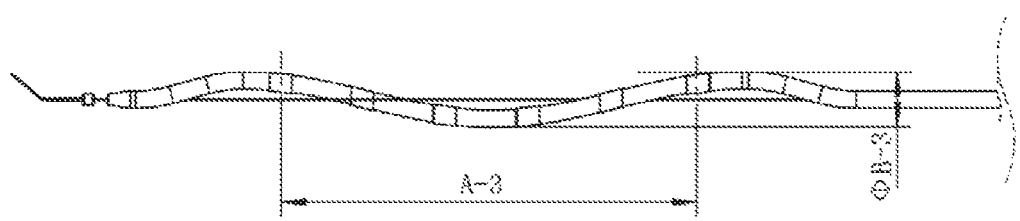
FIG. 22 is a schematic diagram of a usage state of the radio-frequency ablation catheter having a spiral structure shown in FIG. 14 in a relatively small vessel.
Figures 23A, 23B:
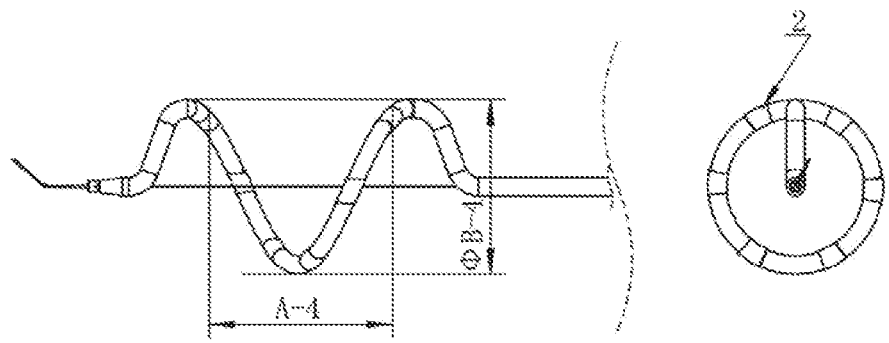
FIG. 23A is a schematic diagram of a usage state of the radio-frequency ablation catheter having a spiral structure shown in FIG. 14 in a relatively large vessel.
FIG. 23B is a schematic side view of the radio-frequency ablation catheter having a spiral structure shown in FIG. 23A.

FIG. 20A to FIG. 23B are schematic diagrams of usage states of the radio-frequency ablation catheter having a spiral structure in lumens of different diameters according to the second embodiment provided in the present invention. As shown in FIG. 20A and FIG. 20B, a radio-frequency ablation catheter for which an initial diameter $\Phi B$ of an electrode support of a spiral shape is 10 mm, an axial distance between the first and the last electrodes is A is used as an example. When the radio-frequency ablation catheter extends into a sheath of $\Phi 2$ mm, a shape of the electrode support is approximate to a straight-line shape, as shown in FIG. 21. When the radio-frequency ablation catheter extends into a vessel of $\Phi 4$ mm from a sheath, the diameter $\Phi B-3$ of the spiral shape of the electrode support is limited by the diameter of the vessel to be approximately 4 mm. In this case, under the effect of natural expansion of the electrode support, the electrode is in close contact with a vessel wall, and the axial distance (A-3) between the first and the last electrodes is greater than A (referring to FIG. 22). As shown in FIG. 23A and FIG. 23B, when the radio-frequency ablation catheter extends into a vessel of $\Phi 12$ mm from a sheath, after the electrode support naturally expands, because the initial diameter $\Phi B$ of the electrode support is less than a diameter of a target lumen, the electrode 2 cannot perform wall attachment. In this case, the diameter of the spiral shape of the electrode support may be increased to $\Phi B-4$ by pulling the wall-attachment adjusting wire 8 backward, which is equal to the diameter of the target lumen, and under the effect of the wall-attachment adjusting wire 8, the multiple electrodes 2 are in close contact with a vessel wall. In this case, the axial distance between the first and the last electrodes is reduced to A-4, and the axial distance between multiple electrodes is reduced, but because the diameter of the target lumen is relatively large, mutual impact between ablation effects of the multiple electrodes may be avoided, thereby avoiding excessive ablation. In addition, as can be further learned from side views shown in FIG. 20B and FIG. 23B, under the effect of the wall-attachment adjusting wire 8, the axial distance between the multiple electrodes 2 that are evenly distributed on the spiral shape of the electrode support is reduced, and a spiral distance is not changed.

In FIG. 20A to FIG. 23B, the electrode support whose $\Phi B$ is 10 mm is used as an example for description. When the initial diameter of the spiral shape of the electrode support is another value (such as 6 mm or 8 mm), similarly, when the electrode support enters a relatively small vessel, under the effect of natural expansion of the electrode support of the spiral shape, the multiple electrodes may be all in a good wall attachment state. When the electrode support enters a target lumen whose diameter is greater than the initial diameter of the spiral shape, as shown in FIG. 23A and FIG. 23B, the multiple electrodes can also be all in close contact with a vessel wall by pulling the wall-attachment adjusting wire, and are in a good wall-attachment state.

Third Embodiment

Figure 24:
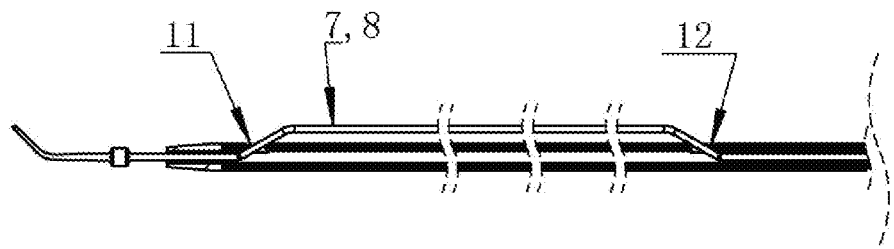
FIG. 24 is a schematic structural diagram of an electrode support and a catheter body in a radio-frequency ablation catheter having a spiral structure according to a third embodiment.
Figure 25:
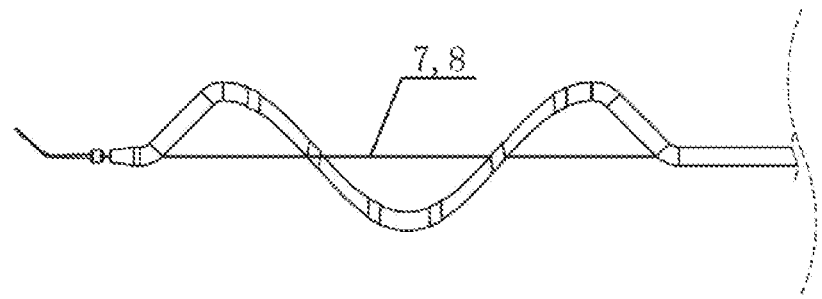
FIG. 25 is a schematic diagram of a usage state of the radio-frequency ablation catheter having a spiral structure shown in FIG. 24.
Figure 26A:
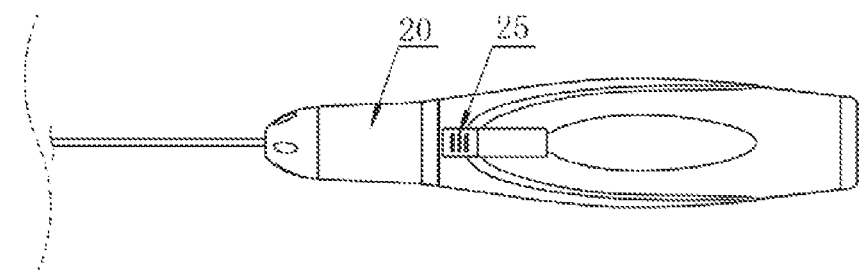
FIG. 26A is a schematic diagram of a usage state of a control handle in the radio-frequency ablation catheter having a spiral structure according to the third embodiment.
Figure 26B:
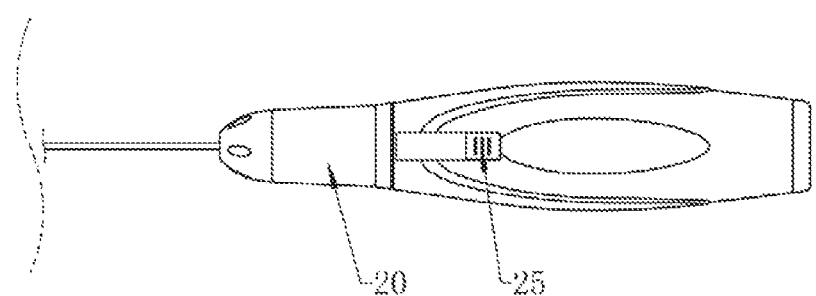
FIG. 26B is a schematic diagram of another usage state of the control handle in the radio-frequency ablation catheter having a spiral structure according to the third embodiment.

A radio-frequency ablation catheter shown in FIG. 24 has a structure similar to that of the radio-frequency ablation catheter in the second embodiment, and for a retraction state of the radio-frequency ablation catheter, refer to FIG. 25. FIG. 26A and FIG. 26B are respectively schematic diagrams of usage states of a control handle 20 of the radio-frequency ablation catheter in different states.

Specifically, a spiral shaped wire 6 is disposed in an electrode support, and a support wire 7 are disposed in a catheter body and the electrode support. A part that is of the support wire 7 and that corresponds to the electrode support is exposed outside the electrode support. A part that is of the support wire 7 and that corresponds to the catheter body is disposed in a particular lumen in the catheter body, and a rear end of the support wire 7 penetrates out of the catheter body and then is fixed on a control component 25 disposed on a control handle 20. The support wire 7 is pulled to change a spiral shape of the electrode support, and the support wire 7 also has a function of a wall-attachment adjusting wire 8. That is, a rear section of the wall-attachment adjusting wire 8 is slidably disposed in a particular lumen in the catheter body, and a rear end of the wall-attachment adjusting wire 8 is connected to the control handle 20. A front section of the wall-attachment adjusting wire 8 penetrates out of the electrode support from a hole 12 and then is exposed outside the electrode support. After the front end of the wall-attachment adjusting wire 8 returns to the interior of the electrode support from a hole 11, the front end of the wall-attachment adjusting wire 8 penetrates out of a front end of the electrode support and is fixed or limited at the outside. The wall-attachment adjusting wire 8 is also a support wire of the catheter body. A developing head and/or a flexible guide wire 9 may be disposed at the front end of the wall-attachment adjusting wire 8.

As shown in FIG. 26A and FIG. 26B, in this embodiment, only one control component 25 connected to the support wire 7 may be disposed on the control handle 20. In this case, the control component 25 is used to adjust a telescopic state of the electrode support. The control component 25 is pushed backward from a location shown in FIG. 26A to a location shown in FIG. 26B, and the support wire 7 may be pulled backward, that is, the wall-attachment adjusting wire 8 is pulled backward, so that the diameter of the spiral shape of the electrode support is increased.

Fourth Embodiment

Figure 27:
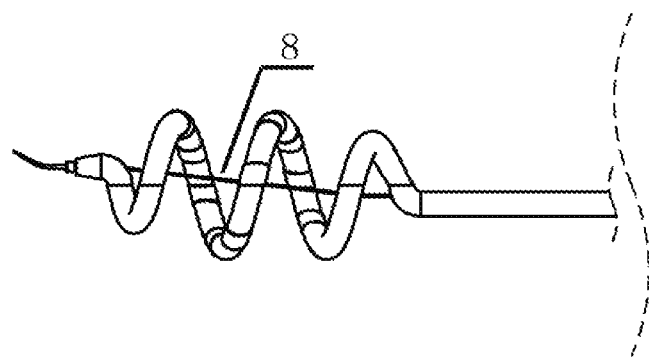
FIG. 27 is a schematic structural diagram of an electrode support and a catheter body in a radio-frequency ablation catheter having a spiral structure according to a fourth embodiment.
Figure 28:
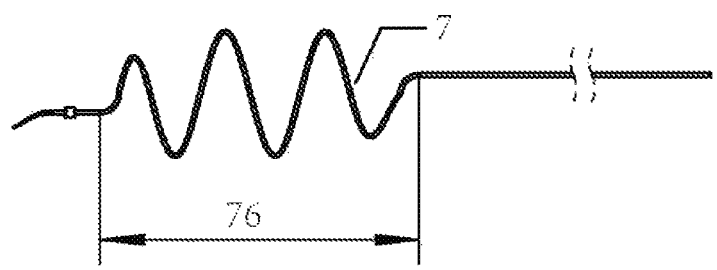
FIG. 28 is a schematic structural diagram of a support wire in the radio-frequency ablation catheter having a spiral structure according to the fourth embodiment.

A radio-frequency ablation catheter shown in FIG. 27 has a structure similar to that of the radio-frequency ablation catheter in the second embodiment. FIG. 28 shows a structure of a support wire 7 in the radio-frequency ablation catheter in the fourth embodiment.

In this embodiment, a structure of a wall-attachment adjusting wire 8 is the same as that in the second embodiment. A rear section of the wall-attachment adjusting wire 8 is slidably disposed in a particular lumen in a catheter body, and a rear end of the wall-attachment adjusting wire 8 is connected to a control component 22 disposed on a control handle 20 or penetrates out of a control handle 20 and then is connected to a control component 22 on a peripheral device. A front section of the wall-attachment adjusting wire 8 penetrates out of an electrode support from a hole 12 and then is exposed outside the electrode support. After the front end of the wall-attachment adjusting wire 8 returns to the interior of the electrode support from a hole 11, the front end of the wall-attachment adjusting wire 8 may be fixed at a front end of the electrode support or may be fixed at a front end of the support wire 7, or may penetrate through corresponding a lumen in the electrode support and the catheter body and return to a rear end of the catheter body, and is fixed on a housing of the control handle 20 or the control component 22 with the rear end of the wall-attachment adjusting wire 8. A diameter of a spiral section of the electrode support may be changed by pulling the control component 22.

In this embodiment, a spiral shaped wire is not independently disposed. As shown in FIG. 28, by means of shaping in advance, a part that is of a front portion of the support wire 7 and that corresponds to the electrode support is shaped to a spiral shape, to form a spiral shaped section 76. The support wire 7 is fixed in a particular lumen in the electrode support and the catheter body, so that a corresponding part of the electrode support may have a spiral shape.

In the second embodiment and the fourth embodiment, the wall-attachment adjusting wire 8 and the support wire 7 may be both disposed in a same lumen in the catheter body, or may be independently disposed in a single lumen in the catheter body respectively.

Fifth Embodiment

Figure 29:
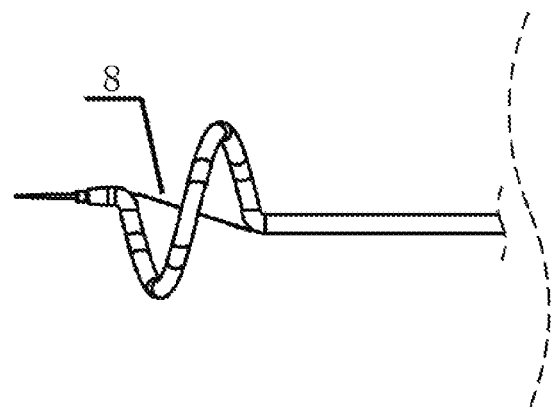
FIG. 29 is a schematic structural diagram of an electrode support and a catheter body in a radio-frequency ablation catheter having a spiral structure according to a fifth embodiment.
Figure 30:
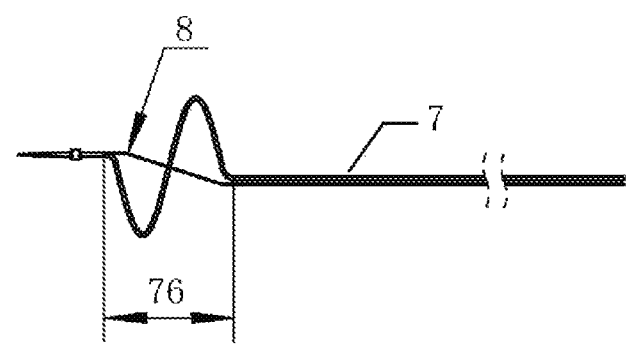
FIG. 30 is a schematic structural diagram of a support wire and a wall-attachment adjusting wire in the radio-frequency ablation catheter having a spiral structure according to the fifth embodiment.

A radio-frequency ablation catheter shown in FIG. 29 has a structure similar to that of the radio-frequency ablation catheter in the second embodiment. FIG. 30 shows structures of a support wire 7 and a wall-attachment adjusting wire 8 in the radio-frequency ablation catheter in the fifth embodiment, where the support wire 7, the wall-attachment adjusting wire 8, and a spiral shaped wire 6 are integrally disposed.

In this embodiment, the support wire 7 is disposed in a catheter body and an electrode support, and a spiral shaped wire is not independently disposed in the electrode support. As shown in FIG. 30, by means of shaping in advance, a part that is a front portion of the support wire 7 and that corresponds to the electrode support is shaped to a spiral shape, to form a spiral shaped section 76.

The wall-attachment adjusting wire 8 and the support wire 7 are integrally disposed. A front end of the wall-attachment adjusting wire 8 is fixed on the support wire 7, or the wall-attachment adjusting wire 8 is a thin filament that is bifurcated from the support wire 7 to the outside. A front section of the wall-attachment adjusting wire 8 penetrates out of the electrode support from a hole 11 and then is exposed outside the electrode support, and returns to the interior of the electrode support/the catheter body from a hole 12. Then, a rear section of the wall-attachment adjusting wire 8 slidably penetrates through a particular lumen in the catheter body and returns to a rear end of the catheter body, and is fixed on a control component 22. A diameter of a spiral section of the electrode support may be changed by pulling the control component 22.

In this embodiment, the rear section of the wall-attachment adjusting wire 8 and the support wire 7 may be both disposed in a particular lumen in the catheter body, or may be independently disposed in another lumen in the catheter body.

Sixth Embodiment

Figures 31A, 31B:
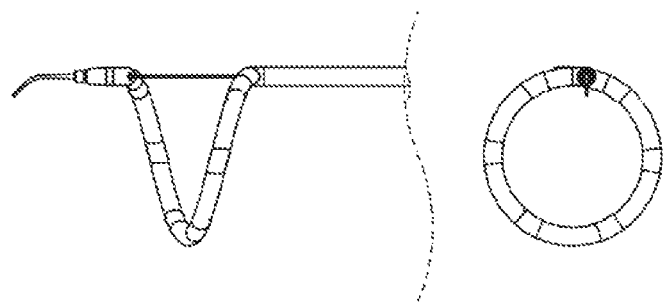
FIG. 31A is a schematic structural diagram of an electrode support and a catheter body in a radio-frequency ablation catheter having a spiral structure according to a sixth embodiment.
FIG. 31B is a schematic side view of the radio-frequency ablation catheter having a spiral structure shown in FIG. 31A.

FIG. 31A and FIG. 31B are schematic structural diagrams of a radio-frequency ablation catheter according to the sixth embodiment.

As shown in FIG. 20B and FIG. 23B, in the second embodiment and the fifth embodiment, even though the wall-attachment adjusting wire 8 is disposed in an eccentric lumen in the catheter body, a part that is of the wall-attachment adjusting wire 8 and that is exposed outside the electrode support is still located near a central location of the spiral shape of the electrode support. When the wall-attachment adjusting wire 8 is pulled backward, the electrode support retracts axially, and the wall-attachment adjusting wire 8 penetrates through the central location of the spiral shape. When the spiral shape of the electrode support is pulled to be approximate to a straight line, the part that is of the wall-attachment adjusting wire 8 and that is exposed outside the electrode support is almost parallel to the outer tube 1 of the electrode support.

Different from the second embodiment to the fifth embodiment, in the sixth embodiment, a wall-attachment adjusting wire 8 is not disposed near a central location of an electrode support of a spiral shape, but is disposed, in an eccentric manner, at a location on an outer circumference of the spiral shape. As shown in FIG. 31A and FIG. 31B, when the wall-attachment adjusting wire 8 is disposed, in an eccentric manner, at a location on the outer circumference of the spiral shape of the electrode support, a part that is of the wall-attachment adjusting wire 8 and that is exposed outside the electrode support does not penetrates through the interior of the spiral shape, but is wound around an outer side of the spiral shape. When the wall-attachment adjusting wire 8 is pulled backward, one circle of spiral section or more than one circle of spiral section located between the holes 11 and 12 in the electrode support retracts and deforms, and a new spiral shape is obtained, so as to increase an existing diameter of the spiral shape, and increase the diameter.

By means of this setting manner, the diameter of the retracted spiral shape can be greatly increased. In an ideal case, the electrode support can adapt to a vessel whose diameter is greater than a diameter of a single spiral section of the electrode support. Because a range of a diameter of a human vessel is fixed, an initial diameter of the spiral shape of the electrode support in the radio-frequency ablation catheter can be reduced, so that it is convenient for the radio-frequency ablation catheter to enter a vessel and move in the vessel.

Seventh Embodiment

FIG. 32A to FIG. 34B are schematic structural diagrams of a radio-frequency ablation catheter according to the seventh embodiment of the present invention. There is a fixing point between a part of a wall-attachment adjusting wire 8 that is exposed outside an electrode support and the electrode support. A front end and a rear end of the wall-attachment adjusting wire 8 both penetrate out of a rear end of a catheter body and are fixed on a control handle 20 or are externally disposed on corresponding control components outside an control handle 20.

Figures 32A, 32B:
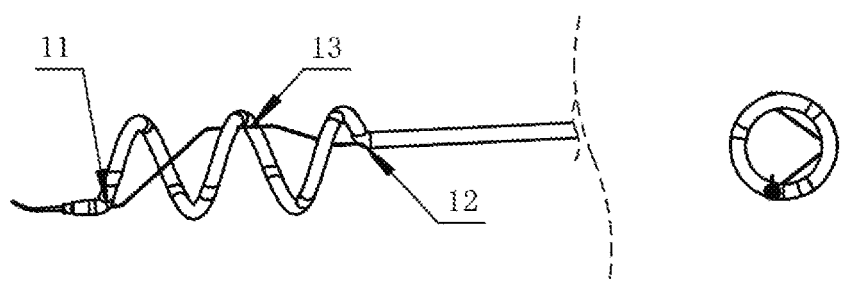
FIG. 32A is a schematic structural diagram of an electrode support and a catheter body in a radio-frequency ablation catheter having a spiral structure according to a seventh embodiment.
FIG. 32B is a schematic side view of the radio-frequency ablation catheter having a spiral structure shown in FIG. 32A.

As shown in FIG. 32A and FIG. 32B, when the wall-attachment adjusting wire 8 is not pulled tight, the part that is of the wall-attachment adjusting wire 8 and that is exposed outside the electrode support is loose. A particular point of the wall-attachment adjusting wire 8 that is exposed outside the electrode support is fixed on a particular spiral section of the electrode support, and the point may be directly fixed on an outer tube or may be fixed in a hole in an outer tube. To maintain a smooth outer wall of the electrode support and prevent a fixing point from scratching a target lumen, disposition of the fixing point in the hole in outer tube 1 is recommended.

Figure 33:
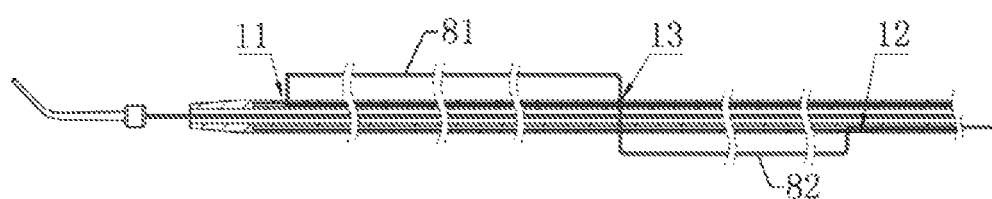
FIG. 33 is a schematic diagram of an internal structure of the electrode support in the radio-frequency ablation catheter having a spiral structure according to the seventh embodiment.

Specifically, as shown in FIG. 33, in this embodiment, there is a fixing point 13 between the wall-attachment adjusting wire 8 and a middle portion of the electrode support. A front section 81 of the wall-attachment adjusting wire 8 is wound forward around the outside of the electrode support from the fixing point 13, returns to the interior of the electrode support from a hole 11 that is close to a front end of the electrode support, and returns to the interior of the control handle 20 through a lumen in the electrode support and the catheter body. A rear section 82 of the wall-attachment adjusting wire 8 is wound backward around the outside of the electrode support from the fixing point 13, returns to the interior of the electrode support from a hole 12 that is close to a rear end of the electrode support, and returns to the interior of the control handle 20 through a lumen in the electrode support and the catheter body. The front section 81 and the rear section 82 of the wall-attachment adjusting wire 8 may return to the control handle 20 through a same lumen in the electrode support and the catheter body, or may respectively return to the control handle 20 through different lumens, as shown in FIG. 33. One control component may be disposed on the control handle 20 and is used to fix the end of the front section 81 of the wall-attachment adjusting wire 8 and the end of the rear section 82 of the wall-attachment adjusting wire 8. Alternatively, two control components may be disposed and are used to respectively fix the end of the front section 81 of the wall-attachment adjusting wire 8 and the end of the rear section 82 of the wall-attachment adjusting wire 8, so as to respectively control the front section 81 and the rear section 82 of the wall-attachment adjusting wire 8.

Figures 34A, 34B:
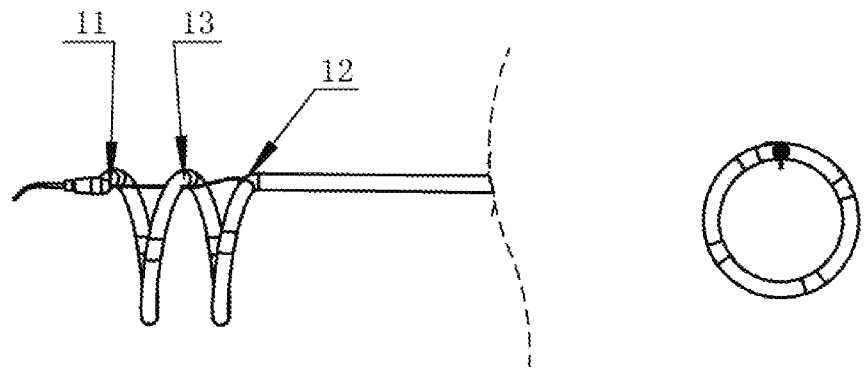
FIG. 34A is a schematic state diagram when a wall-attachment adjusting wire is pulled backward and the electrode support performs wall attachment in the radio-frequency ablation catheter having a spiral structure according to the seventh embodiment.
FIG. 34B is a schematic side view of the radio-frequency ablation catheter having a spiral structure shown in FIG. 34A.

The front section 81 of the wall-attachment adjusting wire 8 is used to control to increase diameters of one or more circles of spiral sections that are of the electrode support and that are located between the hole 11 and the fixing point 13. The rear section 82 of the wall-attachment adjusting wire 8 is used to control to increase diameters of one or more circles of spiral sections that are of the electrode support and that are located between the hole 12 and the fixing point 13. As shown in FIG. 34A and FIG. 34B, when the rear section 82 of the wall-attachment adjusting wire 8 is pulled tight, the fixing point 13 is close to the hole 12 in the electrode support, a diameter of one circle of spiral section located between the fixing point 13 and the hole 12 is continuously approximate to an initial diameter $\Phi B$ of the spiral shape of the electrode support, so that a better wall attachment effect is obtained. More than one circle of spiral section deforms to a new spiral shape, and a diameter of the new spiral shape exceeds the initial diameter $\Phi B$ of the spiral shape of the electrode support, so that the diameter is increased. Similarly, when the front section 81 of the wall-attachment adjusting wire 8 is pulled tight, the hole 11 in the electrode support is close to the fixing point 13, a diameter of one circle of spiral section located between the hole 11 and the fixing point 13 is continuously approximate to the initial diameter $\Phi B$ of the spiral shape of the electrode support, so that a better wall attachment effect is obtained. More than one circle of spiral section deforms to a new spiral shape, and a diameter of the new spiral shape also exceeds the initial diameter $\Phi B$ of the spiral shape of the electrode support, so that the diameter is increased, and a larger diameter for wall attachment and a better wall attachment effect are obtained.

The front section 81 and the rear section 82 of the wall-attachment adjusting wire may be respectively controlled by two single control components correspondingly connected to the front section 81 and the rear section 82, so as to independently adjust a diameter of a different part on the electrode support; or may be controlled together by a same control component, so as to control increase of an overall diameter of multiple spiral sections of the electrode support. In addition, when the end of the front section 81 of the wall-attachment adjusting wire and the end of the rear section 82 of the wall-attachment adjusting wire are respectively fixed on different control components, if the front section 81 and the rear section 82 of the wall-attachment adjusting wire are pulled at the same time, different parts of the electrode support may deform at the same time, so as to adjust a diameter of an entire electrode support, to make the electrode support achieve an axial detraction effect shown in FIG. 34A. Therefore, a spiral diameter after the diameter is increased can achieve an effect shown in FIG. 34B. The front section 81 and the rear section 82 of the wall-attachment adjusting wire 8 may be used to respectively control diameter increase of one or more circles of spiral sections that are of the electrode support and that are located between the hole 12 and the fixing point 13, and located between the hole 11 and the fixing point 13. Therefore, an increased diameter is equal to or even greater than the initial diameter shown in FIG. 32B, so that a better wall attachment effect can be obtained, and a target lumen whose diameter is changed within a larger range can be considered.

Eighth Embodiment

In the eighth embodiment, a wall-attachment adjusting wire 8 disposed in a radio-frequency ablation catheter is formed by multiple strands of wires. A front end of each strand of wire is fixed on an electrode support; and a rear end is wound around a spiral section of the electrode support from the outside and then enters the interior of the electrode support or a catheter body, and then penetrates out of the end of the catheter body through a lumen in the catheter body and is fixed on a corresponding control component disposed on a control handle 20, or a rear end penetrates through a control handle 20 and then is fixed on a corresponding control component on a peripheral device. The multiple strands of wires are respectively used to independently control diameters of different spiral sections of the electrode support.

Figure 35:
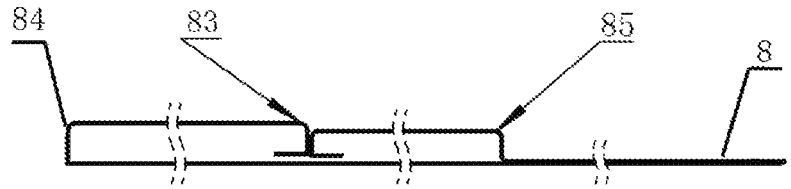
FIG. 35 is a schematic structural diagram of a wall-attachment adjusting wire in a radio-frequency ablation catheter having a spiral structure according to an eighth embodiment.

In a structure shown in FIG. 35, the wall-attachment adjusting wire 8 is formed by two strands of wires 84 and 85. Front ends of the two strands of wires 84 and 85 are fixed together at a particular point on the electrode support, to form a fixing point 83. Rear ends of the two strands of wires 84 and 85 are respectively wound around different spiral sections of the electrode support, enter the interior of the electrode support or the catheter body, return to the rear end through lumens in the electrode support and the catheter body, and are fixed on corresponding control components on the control handle 20. A structure of the wall-attachment adjusting wire 8 having two strands of wires is basically the same as the structure in the seventh embodiment, which can be both used to respectively control diameter increase of spiral sections of a front section and a rear section of the electrode support. Alternatively, the structure in the seventh embodiment may be directly understood as a case in which the wall-attachment adjusting wire 8 in the eighth embodiment uses two strands of wires.

Figure 36A:
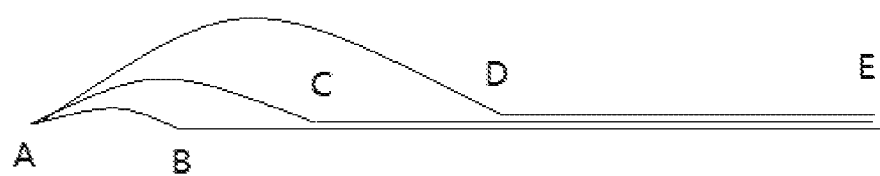
FIG. 36A is another schematic structural diagram of the wall-attachment adjusting wire in the radio-frequency ablation catheter having a spiral structure according to the eighth embodiment.
Figure 36B:
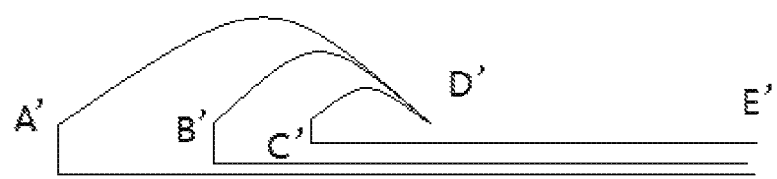
FIG. 36B is still another schematic structural diagram of the wall-attachment adjusting wire in the radio-frequency ablation catheter having a spiral structure according to the eighth embodiment.

When the wall-attachment adjusting wire 8 has more than two strands of wires, a front end of each strand of wire is fixed on the electrode support, a part that is close to the front end (that is, close to the fixing point) is exposed outside the electrode support, a rear end enters the interior of the electrode support from holes provided at different locations on the electrode support, returns to the control handle 20 through a same lumen or different lumens in the electrode support and the catheter body, and is fixed on a corresponding control component. Fixing points of the multiple strands of wires on the electrode support may be the same, may be different, or may be not exactly the same. When the fixing point of the multiple strands of wires on the electrode support are not exactly the same, every two strands of wires may have a common fixing point on the electrode support, and for settings of structures of two strands of wires, refer to the structure shown in FIG. 35. When the fixing point of the multiple strands of wires on the electrode support are the same, as shown in FIG. 36A, front ends of different wires may be fixed at the front end A of the electrode support. Then, rear ends of the strands of wires respectively enter the interior of electrode support from different holes B, C, and D and more holes on the electrode support, and penetrate out of the end of the catheter body through the electrode support and the catheter body. The end E of each of the multiple strands of wires is fixed on a corresponding control component. Alternatively, as shown in FIG. 36B, front ends of different wires may be fixed on a side D' at a rear portion of the electrode support. Then, rear ends of the wires respectively enter the interior of the electrode support from different holes A', B', and C' and more holes that are located on at a front portion of the electrode support, and penetrate out of the end of catheter body through the electrode support and the catheter body. The end E' of each of the multiple strands of wires is fixed on a corresponding control component disposed on the control handle 20 or a corresponding control component on a peripheral device. Each strand of wire enters the interior of the electrode support from a different location on the electrode support, so that a single wire may be pulled to control a change of a diameter of a spiral section between a fixing point located at the front end and a location at which the wire enters the electrode support. Certainly, the foregoing multiple strands of wires may also be fixed on a same control component on the control handle 20, so as to adjust an overall diameter of the electrode support.

When multiple control components are used to respectively control different spiral sections of the electrode support, after the radio-frequency ablation catheter enters a target location, corresponding spiral sections of the electrode support may be expanded section by section according to a requirement, that is, only a spiral section requiring radio frequency is expanded, so as to increase flexibility of adjusting diameters of different spiral sections of the electrode support, and reduce a difficulty of adjusting wall attachment of the radio-frequency ablation catheter.

To sum up, a wall-attachment adjusting wire is disposed in a radio-frequency ablation catheter having a spiral structure, and a diameter of a spiral shape of an electrode support can be changed by pulling the wall-attachment adjusting wire backward, so as to change a wall-attachment state of an electrode, so that the radio-frequency ablation catheter adapts to vessels of different diameters. In addition, the wall-attachment adjusting wire may also use a multi-strand structure, so as to respectively control different spiral sections of the radio-frequency ablation catheter, and reduce a difficulty of diameter adjustment.

In actual clinic treatment, the radio-frequency ablation catheter and the radio-frequency ablation device that are provided in the present invention may be applied to nerve ablation of vessels or tracheas at different parts and vessels or tracheas of multiple different diameters. For example, the radio-frequency ablation catheter and the radio-frequency ablation device are applied to nerve ablation in a renal artery to treat a patient with resistant hypertension, are applied to nerve ablation in a celiac artery to treat a patient with diabetes, for another example, are applied to vagus branch ablation in a trachea/a bronchus to treat an asthmatic patient, and are applied to vagus branch ablation in dodecadactylon to treat a patient with duodenal ulcer. In addition, the radio-frequency ablation catheter and the radio-frequency ablation device may be further applied to nerve ablation in other vessels or tracheas such as a pelvis or a pulmonary artery. It should be noted that, the radio-frequency ablation catheter provided in the present invention is not limited to the foregoing listed applications in clinic treatment, and may be further applied to nerve ablation at other parts.

The radio-frequency ablation catheter having a spiral structure that is provided in the present invention is described above, and the present invention further provides a radio-frequency ablation device including the radio-frequency ablation catheter. In addition to the radio-frequency ablation catheter, the radio-frequency ablation device further includes a radio-frequency ablation host connected to the radio-frequency ablation catheter. A support wall-attachment adjusting wire (and a bifurcated adjusting wire thereof) or a wall-attachment adjusting wire in an electrode support penetrates through a catheter body and then is connected to a corresponding control handle. A shape of the electrode support can be changed by pulling the support wall-attachment adjusting wire by the control handle, so that it is convenient for entering a target lumen, and a wall attachment state in the target lumen is good. The shape of the electrode support can be changed by pulling wall-attachment adjusting wire by the control handle, so that wall-attachment states of the electrode support in target lumens of different diameters are good. In addition, a radio-frequency line and a thermocouple wire in the electrode support are respectively connected to corresponding circuits in the radio-frequency ablation host through the catheter body, so that the radio-frequency ablation host implements radio frequency control and temperature monitoring on multiple electrodes. For settings of the control handle and settings of the radio-frequency ablation host, refer to earlier patent applications disclosed by the applicant, and specific structures of the control handle and the radio-frequency ablation host are not described in detail herein again.

The radio-frequency ablation catheter having a spiral structure and the device thereof that are provided in the present invention are described in detail above. For a person of ordinary skill in the art, any obvious modification made to the present invention without departing from essence and spirit of the present invention shall fall within the protection scope of the present invention.

What is claimed is:

1. A radio-frequency ablation catheter having a spiral structure, comprising an elongated catheter body, wherein an electrode support of a spiral shape is disposed at a front end of the catheter body, multiple electrodes are disposed on the electrode support, and a control handle is disposed at a rear end of the catheter body, wherein
   a slidable support wall-attachment adjusting wire is disposed in one lumen in the electrode support and the catheter body, and the support wall-attachment adjusting wire consists of a flexible section that is distant from the control handle and a rigid section that is near the control handle;
   a head end of the support wall-attachment adjusting wire penetrates through the electrode support, then is limited at a outside of the electrode support, and can move related to the electrode support; a tail end of the support wall-attachment adjusting wire penetrates through the catheter body and is fixed on the control handle; and the control handle is used to control the support wall-attachment adjusting wire to move forward and backward;
   when the electrode support naturally expands to perform wall attachment, a wall attachment status of the electrode can be further adjusted by further pulling the support wall-attachment adjusting wire.

2. The radio-frequency ablation catheter having a spiral structure according to claim 1, wherein
   when the support wall-attachment adjusting wire moves forward to make the rigid section be in the electrode support and the flexible section be at the outside of electrode support, under the effect of the rigid section of the support wall-attachment adjusting wire, a diameter of the spiral shape of the electrode support is reduced, a length is increased and the spiral shape tends to be a straight-line shape; and
   when the support wall-attachment adjusting wire withdraws to make the flexible section be in the electrode support, the electrode support restores to the spiral shape.

3. The radio-frequency ablation catheter having a spiral structure according to claim 2, wherein
   a button control component that is fixed with the tail end of the support wall-attachment adjusting wire is disposed on the control handle, and the support wall-attachment adjusting wire is controlled to move by changing a location of the button control component on the control handle.

4. The radio-frequency ablation catheter having a spiral structure according to claim 1, wherein
   the support wall-attachment adjusting wire has a bifurcated adjusting wire that extends backward; a head end of the bifurcated adjusting wire is fixed at the head end of the support wall-attachment adjusting wire, or a head end of the bifurcated adjusting wire is fixed at a particular part of the flexible section, or the bifurcated adjusting wire is a thin filament that is bifurcated from the flexible section to the outside; and a rear end of the bifurcated adjusting wire penetrates out of a hole provided on an outer tube on the electrode support, penetrates into a hole provided on the electrode support or the catheter body, then extends to the rear end of the catheter with the rigid section of the support wall-attachment adjusting wire side by side through a lumen in the catheter body, enters the interior of the control handle, and is fixed on a second control component.

5. The radio-frequency ablation catheter having a spiral structure according to claim 1, wherein
   a length of the flexible section is not less than a length of an outer tube of the electrode support.

6. The radio-frequency ablation catheter having a spiral structure according to claim 1, wherein
   a straight-head flexible guide wire or a curved-head flexible guide wire is disposed at a front end of the flexible section.

7. The radio-frequency ablation catheter having a spiral structure according to claim 1, wherein
   the flexible section is made of a thin filament whose diameter is less than that of the rigid section; and the flexible section and the rigid section are integrally molded or are assembled by using two thin filaments of different diameters.

8. The radio-frequency ablation catheter having a spiral structure according to claim 1, wherein
   the flexible section uses a spring structure or a flexible tube structure.

9. The radio-frequency ablation catheter having a spiral structure according to claim 1, wherein
   a spiral shaped wire is disposed in the electrode support.

10. A radio-frequency ablation catheter having a spiral structure, comprising an elongated catheter body, wherein an electrode support of a spiral shape is disposed at a front end of the catheter body, one or more electrodes are disposed on the electrode support, and a control handle is disposed at a rear end of the catheter body, wherein a wall-attachment adjusting wire is formed by multiple strands of wires; a front end of each strand of wire is fixed on the electrode support; a part near the front end is exposed outside the electrode support; a rear end of each strand of wire enters an interior of the electrode support from holes provided at different locations on the electrode support, and then arrives at the distal end of the catheter body through a lumen in the catheter body, and is fixed on a corresponding control component disposed on the control handle; and the multiple strands of wires are respectively used to control diameters of different spiral sections between a fixing point located at the front end and a location at which the wire enters the electrode support independently.

11. The radio-frequency ablation catheter having a spiral structure according to claim 10, wherein fixing points of the multiple strands of wires on the electrode support are different from each other.

12. The radio-frequency ablation catheter having a spiral structure according to claim 10, wherein every two strands of wires have a common fixing point on the electrode support.

13. The radio-frequency ablation catheter having a spiral structure according to claim 10, wherein each strand of wire enters the interior of the electrode support from a different location on the electrode support.

14. The radio-frequency ablation catheter having a spiral structure according to claim 10, wherein fixing points of the multiple strands of wires on the electrode support are the same.

* * * * *